United States Patent [19]
Bishop

[11] Patent Number: 5,874,666
[45] Date of Patent: Feb. 23, 1999

[54] SPINDLE QUICK-CONNECT AND ROTARY VISCOMETER

[75] Inventor: Robert P. Bishop, Pembroke, Mass.

[73] Assignee: Brookfield Engineering Laboratories, Stoughton, Mass.

[21] Appl. No.: 934,576

[22] Filed: Sep. 19, 1997

[51] Int. Cl.⁶ .................................................. G01N 11/14
[52] U.S. Cl. ........................................ 73/54.35; 73/54.28
[58] Field of Search ............................... 73/54.35, 54.23, 73/54.28

[56] References Cited

U.S. PATENT DOCUMENTS

| | | | |
|---|---|---|---|
| 5,201,214 | 4/1993 | Sekiguchi et al. | 73/54.35 |
| 5,287,732 | 2/1994 | Sekiguchi | 73/54.35 X |

FOREIGN PATENT DOCUMENTS

| | | | |
|---|---|---|---|
| 2-231549 | 9/1990 | Japan | 73/54.35 |
| 972328 | 11/1982 | U.S.S.R. | 73/54.35 |

*Primary Examiner*—Daniel S. Larkin
*Attorney, Agent, or Firm*—Jerry Cohen

[57] ABSTRACT

Viscometer shaft coupling with upper shaft assembly (12) and lower shaft assembly (14), with overlapping flat ends thereat a diametral plan and constrained by a slidable sleeve (16) overlapping the shafts.

5 Claims, 1 Drawing Sheet

SPINDLE QUICK-CONNECT AND ROTARY VISCOMETER

FIELD AND BACKGROUND OF THE INVENTION

The present invention relates to rotary viscometers and like instruments, tools and machines with high speed rotation of a load (such as a spindle, suspended at a shaft end), at variable torque that have frequent changes and more particularly to a drive shaft split longitudinally into two parts, an arrangement enabled by the combination of parts set forth below.

Rotary viscometers are a class of viscosity measuring instruments that have a shaft (usually vertically arranged) suspending a spindle or other measuring end piece such as a spindle or disk in a fluid whose viscosity is to be measured. The spindle or the like is rotated by the shaft at high speed and creates a torque loading (dependent on fluid viscosity) transmitted through the shaft to a transducer for generating an output reading or control signal.

Often, multiple, quick changes of the spindle or the like are required and the need is met inadequately by threading parts on and off, chucks or like state of the art artifacts.

It is a principal object of the present invention to provide a new approach that meets the need more effectively.

SUMMARY OF THE INVENTION

The present invention comprises a viscometer instrument with a spindle quick connect coupling. The instrument has a high speed drive including a motor and gearing on board driving a principal downwardly extending shaft via a suspension mount. The shaft and suspension mount connect to an upper end of the quick connect coupling. The instrument has a sample fluid container and a lower end mounting cone, disc or spindle rotating part that rotates therein. The rotating part is held by a lower end of the quick connect coupling. The upper and lower end of the quick connect coupling have matching flat angled surfaces and a surrounding sleeve or other means of holding them together. The holding means prevents the upper and lower parts from spreading and from moving axially with respect to each other beyond a limited planned axial slippage. The angle of the two surfaces can vary from 2° to 20° but is preferably about 5° relative to the axis of the shaft.

The flat surfaces can be hard and machined to a precision of 16–32 micro inches (400–800 micrometers). To the extent the surfaces may wear, there will only be a slight axial relative sliding on the order of 0.020 in. (0.5 mm) well within the range of tolerance of axial position of the rotating part of the viscometer instrument. A sleeve form of holder is of a hard material and mounted to slide on and off axially over the coupling. But other forms of coupling can be used including clamps or bolts.

The lower coupling part can be a series of such parts of different lengths and/or mounting different types of rotating parts. These are easily and quickly interchangeable by displacing the sleeve or other lock.

Frequent interchanges are not accompanied by threading pieces on and off or by a need to work an alignment or length adjustment and disturbance of delicate parts of the suspension mount.

Other objects, features and advantages will be apparent from the following detailed description of preferred embodiments taken in conjunction with the accompanying drawings in which:

BRIEF DESCRIPTION OF PREFERRED EMBODIMENTS

Figures 1, 2:
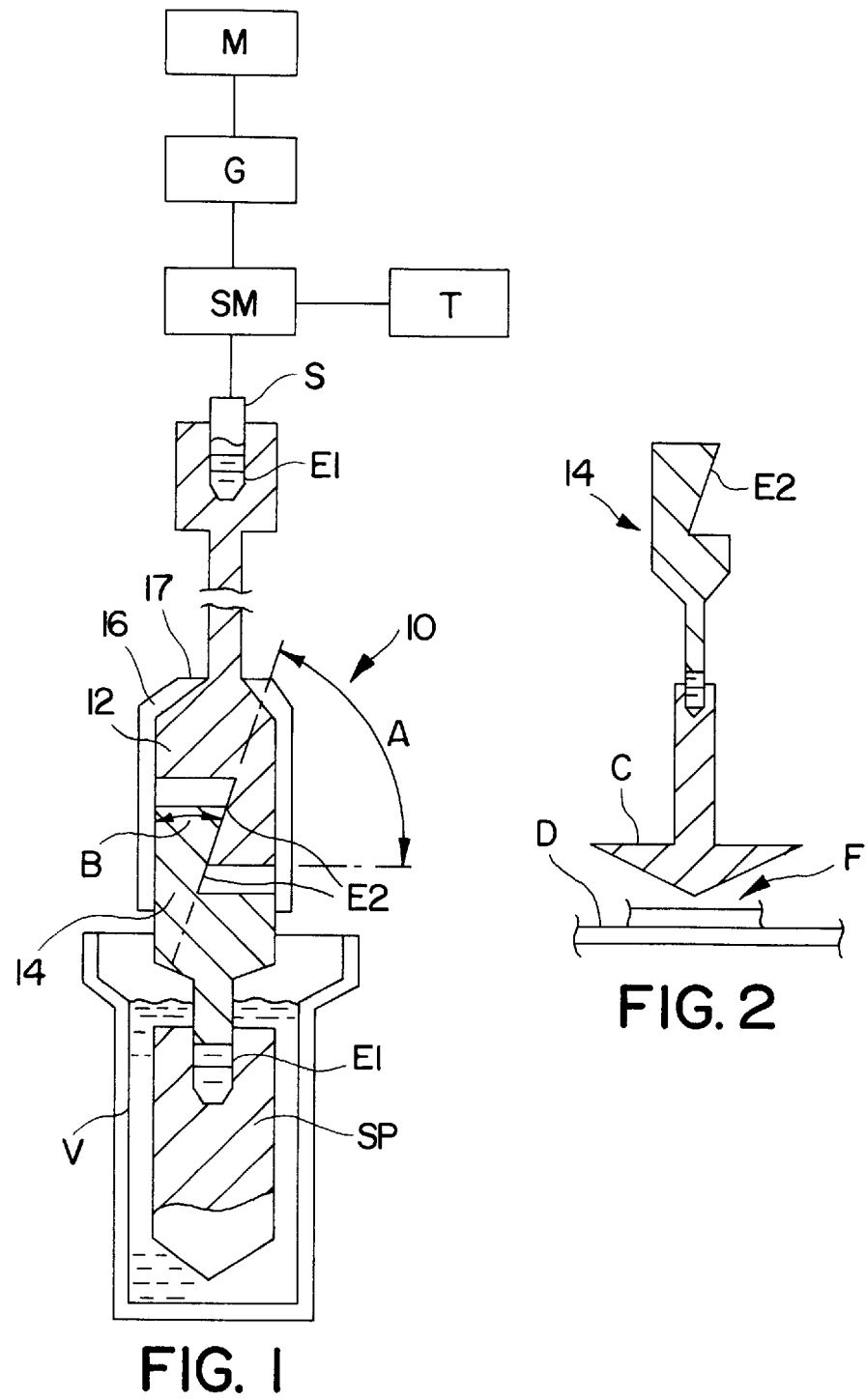
FIG. 1 shows a preferred embodiment of the improved viscometer of this invention.
FIG. 2 shows an interchangeable form of viscosity responsive usable in the FIG. 1 apparatus.

A viscometer V comprises a motor drive M, gearing G, and a suspension mounting SM of a shaft driven by the motor and gearing. A transducer T is responsive to torque loading on the shaft and suspension mount. A spindle SP is coupled to the shaft and rotatable in a can or other container of fluid F whose viscosity is to be measured. The coupling 10 between the shaft and spindle comprises an upper section 12 and a lower section 14, each of which is in the form of a stepped shaft with an attaching end E1 (e.g. threads) and a diametral flat end E2 at an angle B to axial direction of 2°–20° preferably 5°. The angle can also be defined as an angle A relative to a plane orthogonal to the axis, i.e. 88°–70° preferably 85°. The length of the flat is at least equal to the shaft diameter and preferably over two times the shaft diameter. A slidable sleeve 16 fits over the assembled coupling parts 12, 14 and holds them together.

The sleeve can be lifted upwardly to allow a quick change to another type of member for interacting with fluid—e.g. a differently dimensioned or weighted spindle or a different device type such as cone C for cone/disk (D) viscometry measurement (FIG. 2). The sleeve is then dropped to capture the newly inserted part. Preferably, all coupling parts are made of hard steels. Sleeve 16 rotates with parts 12, 14.

The weight hanging from the coupling keeps the connection straight. The mating flat surfaces provide a full rotation of driving force from S to SP (or C). The flat surfaces are precision machined to within a 16–32 micro inch range for running true. The round outer surfaces of sections 12 and 14 are machined to 32 microinches. To the extent that wear may occur at the flats or diameters, section 14 slides down expanding the effective diameter of its overlap with 12 and against the inside of 16 thereby creating a new tight fit 40 of the coupling. Such 'slippage' if it occurs at all, noticeably, would be on the order of under 0.5 mm. length, too little to affect significantly SP or C clearances with a surface below them.

Either of parts 12, 14 can be made of a ¾ in. long (excluding the reduced diameter attachment portions) slightly less than 0.3 inch diameter shaft that has 0.4–0.5 inch of its length flattened as described above, preferably to an angle (B) of 5° plus or minus 0.1 degree and with a 16 micro inch surface roughness, the round outer surface being flattened to 32 micro inch. The angle B flat crosses the diametral plane of the shaft half way above the length of the flat. A sleeve to fit two such head-to-toe assembled coupling parts would be a tube of about one inch length, 0.3 inch I.D. and having a collar 17 (FIG. 1). Thus the assembly 12, 14 is initially slightly less than 0.3 inches O.D. without the sleeve 16 or as the sleeve slides down while 14 and its load are manually held up. The 14 and its load are allowed to drop to where the overlapping sections of 12, 14 have an effective O.D. of 0.3 in.

For disassembly, the user lifts the load and part 14 to raise the same and thereby loosen sleeve 16 which can then be raised to allow removal of part 14 and its load. Another part can then be interchangeably attached to the instrument.

Several variances can be made within the scope of the invention. For example, the threaded ends E2 can be replaced by various forms of a permanent or semi-permanent attachment. The invention is also usable in other contexts than viscometry, e.g. rotating tools and machinery, fans, moveable displays, and clutches.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A viscometer comprising:
   (a) a rotatable fluid viscosity responsive part attached to a rotating shaft via a coupling,
   (b) the coupling comprising:
      (1) an upper shaft section with a flat end,
      (2) a lower shaft section essentially axially aligned with the upper section and with a flat end for overlapping the upper section's flat end to form therewith a plane that passes through a diametral plane of the section at n angle of 2°–20°, and
      (3) a sleeve overlapping the upper and lower shaft sections to hold the sections together; the said sections and sleeve being constructed and arranged so that the lower section slips slightly axially to bind into the sleeve.

2. Viscometer in accordance with claim 1, wherein the angle is 4°–8°.

3. Viscometer in accordance with claim 1, wherein the surface finish of the flats of the sections are finer than on their round outer surfaces.

4. Viscometer in accordance with claim 1, wherein the length overlap of the flats is at least equal to one diameter.

5. Viscometer in accordance with claim 4, wherein the length overlap of the flats is at least equal to two diameters.

* * * * *